US011848096B2

(12) United States Patent
Caffarel et al.

(10) Patent No.: US 11,848,096 B2
(45) Date of Patent: Dec. 19, 2023

(54) HOME VISIT ASSESSMENT AND DECISION SUPPORT SYSTEM

(71) Applicant: KONINKLIJKE PHILIPS N.V., Eindhoven (NL)

(72) Inventors: Jennifer Caffarel, Eindhoven (NL); Gijs Geleijnse, Geldrop (NL)

(73) Assignee: Koninklijke Philips N.V., Eindhoven (NL)

( * ) Notice: Subject to any disclaimer, the term of this patent is extended or adjusted under 35 U.S.C. 154(b) by 473 days.

(21) Appl. No.: 16/084,609

(22) PCT Filed: Mar. 17, 2017

(86) PCT No.: PCT/EP2017/056398
§ 371 (c)(1),
(2) Date: Sep. 13, 2018

(87) PCT Pub. No.: WO2017/158160
PCT Pub. Date: Sep. 21, 2017

(65) Prior Publication Data
US 2019/0074085 A1    Mar. 7, 2019

Related U.S. Application Data

(60) Provisional application No. 62/309,482, filed on Mar. 17, 2016.

(51) Int. Cl.
*G16H 40/20*      (2018.01)
*G16H 10/20*      (2018.01)
(Continued)

(52) U.S. Cl.
CPC ........... *G16H 40/20* (2018.01); *G06F 3/0482* (2013.01); *G16H 10/20* (2018.01); *G16H 10/60* (2018.01); *G16H 50/20* (2018.01); *G16H 50/30* (2018.01)

(58) Field of Classification Search
CPC ........ G16H 40/20; G16H 10/60; G16H 50/30; G16H 10/20; G16H 50/20; G06F 3/0482
(Continued)

(56) References Cited

U.S. PATENT DOCUMENTS 5,544,649 A   *   8/1996   David ..................... G16H 80/00
                                                      600/587
9,501,919 B2 *   11/2016   Laett .................. G08B 21/0476
(Continued)

FOREIGN PATENT DOCUMENTS

EP            531889 A2      3/1993
WO      2014049527 A2     4/2014
(Continued)

OTHER PUBLICATIONS

C. Kamel Boulos, et al., "Crowdsourcing, citizen sensing and sensor web technologies for public and environmental health surveillance and crisis management: Trends, OGC standards and application examples", . International Journal of Health Geographics, 10, 67, 2011. (Year: 2011).*

*Primary Examiner* — Amber A Misiaszek

(57) ABSTRACT

This disclosure describes a system that standardizes collection of home health observations during a home visit by a caregiver. The system causes display of a graphical user interface to the caregiver. The graphical user interface comprises observation fields that receive home health observations about conditions in the home, and a display field that displays a virtual representation of the home conditions. The system is configured to store the home health observations and the virtual representation in a subject profile for the subject that is part of a database of home health observations and virtual representations for a plurality of subjects, compare the home health observations and virtual representation to previous home health observations and previous virtual representations for similar subjects, determine suggested (Continued)

questions for the caregiver to ask the subject, update a care plan for the subject, and determine health recommendations for the subject.

20 Claims, 7 Drawing Sheets

(51) Int. Cl.
    *G16H 50/20*     (2018.01)
    *G16H 10/60*     (2018.01)
    *G16H 50/30*     (2018.01)
    *G06F 3/0482*     (2013.01)

(58) Field of Classification Search
    USPC .......................................................... 705/2–3
    See application file for complete search history.

(56) References Cited

U.S. PATENT DOCUMENTS

| | | | |
|---|---|---|---|
| 2006/0033625 A1 | 2/2006 | Johnson et al. | |
| 2007/0232942 A1* | 10/2007 | Quy | A63B 71/0622 |
| | | | 600/508 |
| 2007/0276701 A1 | 11/2007 | Suzuki et al. | |
| 2008/0059242 A1* | 3/2008 | Stanford | G16H 10/60 |
| | | | 707/999.107 |
| 2008/0084296 A1* | 4/2008 | Kutzik | G08B 21/0453 |
| | | | 340/540 |
| 2010/0198608 A1* | 8/2010 | Kaboff | G16H 40/67 |
| | | | 715/741 |
| 2010/0324927 A1 | 12/2010 | Tinsley | |
| 2011/0105853 A1* | 5/2011 | Rakowski | G06Q 10/10 |
| | | | 600/300 |
| 2011/0238446 A1 | 9/2011 | Chaudhry | |
| 2013/0030837 A1 | 1/2013 | Ackerson et al. | |
| 2013/0187768 A1* | 7/2013 | Eisterhold | G08C 19/00 |
| | | | 340/12.53 |
| 2014/0081659 A1* | 3/2014 | Nawana | A61B 5/4833 |
| | | | 705/3 |
| 2014/0222460 A1 | 8/2014 | Bischoff et al. | |
| 2014/0229199 A1 | 8/2014 | Beckley | |
| 2016/0324460 A1* | 11/2016 | Kusens | A61B 5/1128 |
| 2021/0186329 A1* | 6/2021 | Tran | A43B 3/42 |

FOREIGN PATENT DOCUMENTS

| | | |
|---|---|---|
| WO | 2014135699 A2 | 9/2014 |
| WO | 2015198180 A1 | 12/2015 |

\* cited by examiner

HOME VISIT ASSESSMENT AND DECISION SUPPORT SYSTEM

CROSS-REFERENCE TO PRIOR APPLICATIONS

This application is the U.S. National Phase application under 35 U.S.C. § 371 of International Application No. PCT/EP2017/056398, filed on 17 Mar. 2017, which claims the benefit of U.S. Provisional Patent Application No. 62/309482, filed on 17 Mar. 2016. These applications are hereby incorporated by reference herein.

BACKGROUND

1. Field

The present disclosure pertains to a system and method for standardizing collection of home health observations made during a home visit by a caregiver to a home of a subject.

2. Description of the Related Art

Home health caregivers believe that gathering information about a patient's home situation is essential for profiling the patient and creating an appropriate care plan. Health plan administrators and home health agencies, for example, invest in intake meetings at the home of the patient. During such a visit, the home situation of the patient is assessed, but is typically not formally recorded or widely shared.

SUMMARY

Accordingly, one or more aspects of the present disclosure relate to a system configured to standardize collection of home health observations during a home visit by a caregiver to a home of a subject. The system comprises one or more hardware processors and/or other components. The one or more hardware processors are configured by machine-readable instructions to: cause display of a graphical user interface to the caregiver on a computing device associated with the caregiver while the caregiver is in the home of the subject, the graphical user interface comprising one or more observation fields configured to receive entry and/or selection of the home health observations from the caregiver about conditions in the home of the subject, and a display field configured to display a virtual representation of the home conditions to the caregiver; receive the home health observations from the caregiver via the one or more observation fields; and generate the virtual representation of the home conditions for display to the caregiver via the display field based on the home health observations, the virtual representation of the home conditions comprising an aggregation of the home health observations.

Another aspect of the present disclosure relates to a method for standardizing collection of home health observations with a standardization system during a home visit by a caregiver to a home of a subject. The system comprises one or more hardware processors and/or other components. The method comprises: causing, with the one or more hardware processors, display of a graphical user interface to the caregiver on a computing device associated with the caregiver while the caregiver is in the home of the subject, the graphical user interface comprising one or more observation fields configured to receive entry and/or selection of the home health observations from the caregiver about conditions in the home of the subject, and a display field configured to display a virtual representation of the home conditions to the caregiver; receiving, with the one or more hardware processors, the home health observations from the caregiver via the one or more observation fields; and generating, with the one or more hardware processors, the virtual representation of the home conditions for display to the caregiver via the display field based on the home health observations, the virtual representation of the home conditions comprising an aggregation of the home health observations.

Still another aspect of present disclosure relates to a system for standardizing collection of home health observations during a home visit by a caregiver to a home of a subject. The system comprises: means for causing display of a graphical user interface to the caregiver on a computing device associated with the caregiver while the caregiver is in the home of the subject, the graphical user interface comprising one or more observation fields configured to receive entry and/or selection of the home health observations from the caregiver about conditions in the home of the subject, and a display field configured to display a virtual representation of the home conditions to the caregiver; means for receiving the home health observations from the caregiver via the one or more observation fields; and means for generating the virtual representation of the home conditions for display to the caregiver via the display field based on the home health observations, the virtual representation of the home conditions comprising an aggregation of the home health observations.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
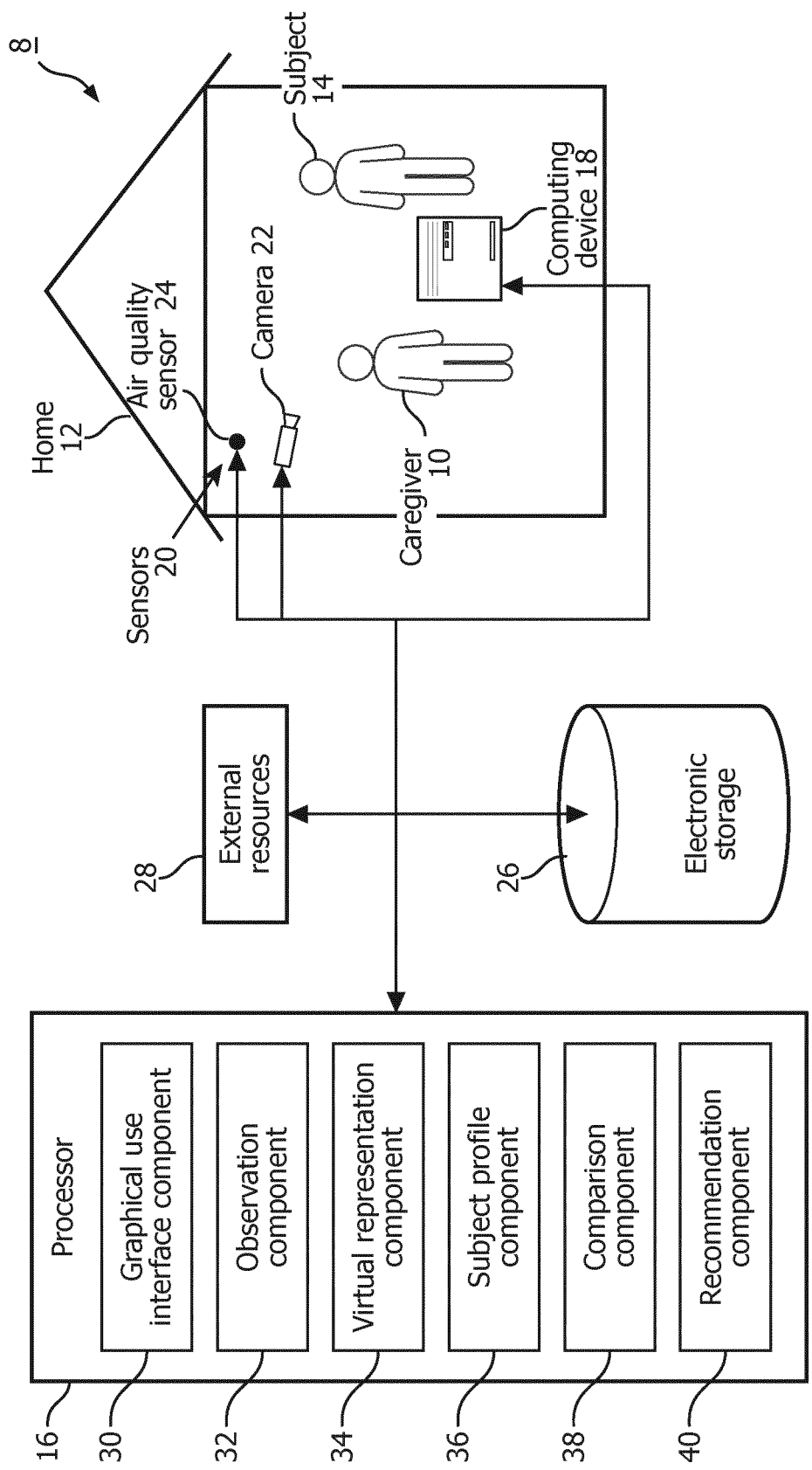
FIG. 1 is a schematic illustration of a system configured to standardize collection of home health observations made during a home visit by a caregiver to a home of a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 8 configured to standardize collection of home health observations made during a home visit by a caregiver 10 to a home 12 of a subject 14. Healthcare often focuses on diagnosing and treating a clinical condition. However, socio-economic and lifestyle conditions are considered to be the main contributors to the occurrence and status of chronic conditions. There is an increasing belief that by addressing these factors, one can support medical treatment and act as a preventive measure for potential future health issues. Questionnaires aiming to assess lifestyle are basic and cover aspects such as smoking, physical activity, and diet (e.g., the NHS Lothian lifestyle questionnaire). These questionnaires are useful when looking for specific information and/or setting goals. However misleading information may be given by the person filling in the questionnaire.

Unfortunately, assessing a person's lifestyle may be difficult. For example, subject 14 may be seen in a formal, non-familiar environment such as a clinic, whereby little information other than that given by subject 14 themselves can be derived. During a medical consultation, subjects are often asked about their lifestyle, whether they are physically active, eat healthily, etc. However, the report from a given subject may be biased, incorrect and/or incomplete, either with the deliberate purpose of dissimulating the lifestyle from the clinician, and/or due to a difference in perception by the subject in as to what constitutes a healthy lifestyle.

Medical and/or social care staff (e.g., caregiver 10) visiting a subject (e.g., subject 14) in their home environment (e.g., home 12) often report that they have a much better feel and/or understanding for who the subject is and that this helps them in diagnosis and/or care delivery. This may be due to the fact that subjects feel more comfortable in a familiar environment, but it also may stem from the fact that caregiver 10 may gather information from the surroundings, and/or the fact that the caregiver is able to assess and verify information in a better way. For example, self-reported healthy eating behavior can be verified by inspecting the contents of the fridge. The surroundings provide caregiver 10 a context which may help caregiver 10 interpret information given by subject 14, and/or the surroundings may provide information in their own right, without subject 14 needing to provide information about their surroundings themselves.

Unfortunately, with present homecare systems this valuable information is rarely reported (e.g., due to the contextual nature of the information) and is difficult to share with peer medical and/or social care staff (e.g., other caregivers) because such information often varies widely for different subjects and is difficult to record in an organized way. Furthermore, intuitive knowledge builds with time and experience visiting multiple subjects and is not easily transferred to less experienced personnel. Present electronic systems do not attempt to organize this information, and either collect this information as free text or as answers to pre-defined questionnaires.

System 8 is configured to record and/or present contextual (e.g., home conditions) information such as home health observations and/or virtual representations of home conditions (described below) about home 12 for subject 14 in a substantially standardized way, record the information in a database of contextual (e.g., home conditions) information for multiple subjects and multiple homes, analyze the contextual information for subject 14 and the database information for other subjects such that the information can be used by peer caregivers to add context to other objective and subjective assessments made in home 12 of subject 14 and/or other homes of other subjects, automate decision support for caregiver 10 and/or subject 14, and/or perform other operations. In some embodiments, system 8 is configured to cluster information in the database for similar home assessments and/or associated care plans (described below) for similar subjects to facilitate sharing intuitive knowledge among peer caregivers, coaching less experienced caregivers to notice the important "evidence" during a home visit, checking subject self-reported information for consistency, focusing subject interviews on topics of concern, providing decision support to caregivers (e.g., caregiver 10) for both home assessments and/or care plan creation, and/or other activities.

Caregiver 10 may include medical and/or social care staff; home health staff; nurses; doctors; parents, children, and/or other caregiving relatives; and/or other caregivers. In general, caregiver 10 may include any person capable of visiting home 12 of subject 14 and making observations about the home environment of subject 14. Home 12 may include a permanent home of subject 14, a temporary home of subject 14, and/or any other location where subject 14 spends time when subject 14 is not in a hospital, at a doctor's office, and/or at any other care facility. For example, in some embodiments, home 12 includes a house, an apartment, a hotel room, a nursing home, a vehicle, and/or any other dwelling where subject 14 resides. In some embodiments, system 8 includes one or more of a processor 16, a computing device 18, a sensor 20, electronic storage 26, external resources 28, and/or other components.

Processor 16 is configured to provide information processing capabilities in system 8. As such, processor 16 may comprise one or more of a digital processor, an analog processor, a digital circuit designed to process information, an analog circuit designed to process information, a state machine, and/or other mechanisms for electronically processing information. Although processor 16 is shown in FIG. 1 as a single entity, this is for illustrative purposes only. In some embodiments, processor 16 may comprise a plurality of processing units. These processing units may be physically located within the same device (e.g., a server), or processor 16 may represent processing functionality of a plurality of devices operating in coordination (e.g., a server, computing device 18 associated with caregiver 10, computing devices associated with subject 14 and/or other users, sensors 20, devices that are part of external resources 28, and/or other devices.)

As shown in FIG. 1, processor 16 is configured via machine-readable instructions to execute one or more computer program components. The one or more computer program components may comprise one or more of a graphical user interface component 30, an observation component 32, a virtual representation component 34, a subject profile component 36, a comparison component 38, a recommendation component 40, and/or other components. Processor 16 may be configured to execute components 30, 32, 34, 36, 38, and/or 40 by software; hardware; firmware; some combination of software, hardware, and/or firmware; and/or other mechanisms for configuring processing capabilities on processor 16.

It should be appreciated that although components 30, 32, 34, 36, 38, and 40 are illustrated in FIG. 1 as being co-located within a single processing unit, in embodiments in which processor 16 comprises multiple processing units, one or more of components 30, 32, 34, 36, 38, and/or 40 may be located remotely from the other components. The description of the functionality provided by the different components 30, 32, 34, 36, 38, and/or 40 described below is for illustrative purposes, and is not intended to be limiting, as any of components 30, 32, 34, 36, 38, and/or 40 may provide more or less functionality than is described. For example, one or more of components 30, 32, 34, 36, 38, and/or 40 may be eliminated, and some or all of its functionality may be provided by other components 30, 32, 34, 36, 38, and/or 40. As another example, processor 16 may be configured to execute one or more additional components that may perform some or all of the functionality attributed below to one of components 30, 32, 34, 36, 38, and/or 40.

Graphical user interface component 30 is configured to cause display of the graphical user interface to caregiver 10 and/or other users. The graphical user interface is displayed on computing device 18 and/or other devices. The graphical user interface is displayed on computing device 18 while caregiver 10 is in home 12 of subject 14 and/or at other times. The graphical user interface may be configured to provide an interface between computing device 18 and caregiver 10 through which caregiver 10 may provide information to and receive information from system 8 (e.g., such that caregiver 10 may enter, select, and/or otherwise communicate home health observations to system 8). This enables home health observations, data, cues, results, and/or instructions and any other communicable items, collectively referred to as "information," to be communicated between caregiver 10 and system 8. In some embodiments, the graphical user interface includes a plurality of separate interfaces associated with computing device 18, processor 16 and/or other components of system 8, for example. In some embodiments, the graphical user interface includes at least one interface that is provided integrally with computing device 18. The graphical user interface comprises one or more observation fields configured to receive entry and/or selection of the home health observations from caregiver 10 about conditions in home 12 of subject 14, one or more display fields configured to display a virtual representation of the home conditions to caregiver 10 and/or other users, and/or other fields.

Observation component 32 is configured to receive home health observations about home 12 of subject 14 and/or other information. The home health observations are received from caregiver 10 via the observation fields of the graphical user interface and/or from other sources. In some embodiments, receiving the home health observations includes receiving information related to a diet of subject 14, hygiene of subject 14, whether subject 14 and/or another occupant of home 12 smokes, presence of clutter in home 12, presence of pets in home 12, safety hazards in home 12, appliances and/or furniture present in home 12, a physical arrangement of home 12 and/or furniture and/or appliances in home 12, information related to smells in home 12, physical distances in home 12 (e.g., a distance of a route between bed and a bathroom), information related to tortuosity of various commonly traveled routes within home 12 (e.g., a tortuosity of the route between bed and the bathroom), and/or other characteristics of the home environment of subject 14. In some embodiments, observation component 32 is configured to receive the home health observations wirelessly from computing device 18 and/or in other ways. In some embodiments, observation component 32 is configured to receive the home health observations in substantially real-time as the observations are made, at a later time after the observations are made, and/or at other times.

In some embodiments, observation component 32 is configured to determine home health observations based on the output signals from sensor 20 that convey information related to the physical conditions present in home 12 of subject 14. For example, observation component 32 may determine home health observations based on the images of the home from a camera 22, information from an air quality sensor 24, and/or information from other sensors 20 (described below). In this example, observation component 32 may comprise image processing software configured to detect presence of clutter (e.g., via edge detection filtering), light quality (e.g., via contrast and brightness), and/or other conditions present in home 12. This example is not intended to be limiting, observation component 32 may comprise any software configured to automatically determine physical conditions present in home 12 based on any of the different types of sensors described herein as sensor 20.

Virtual representation component 34 is configured to generate a virtual representation of conditions in home 12. The virtual representation of conditions in home 12 is generated for display to caregiver 10 via the display field of the graphical user interface and/or other displays. The virtual representation is generated based on the home health observations, the output signals, and/or other information. The virtual representation of the home conditions comprises an aggregation of the home health observations, the output signals, and/or other information. The virtual representation may be and/or include a virtual image representative of the environment of home 12, an infographic representative of the home health observations, a visual image of home 12 (e.g., real-time and/or pre-recorded image from sensor 20), descriptors such as labels and/or highlights corresponding to the home health observations on a displayed virtual representation and/or image of home 12 and/or on previously generated reports and/or questionnaires for subject 14 (e.g., if unhealthy foods have been observed in home 12, virtual representation component 34 may control the display field to highlight an uncertainty of healthy eating in an earlier self-report by subject 14 to aid discussion and/or education with subject 14), illustrations of information conveyed by output signals from sensors 20 (e.g., a house temperature, airflow, pollution level, etc.), and/or other information.

Figure 2:
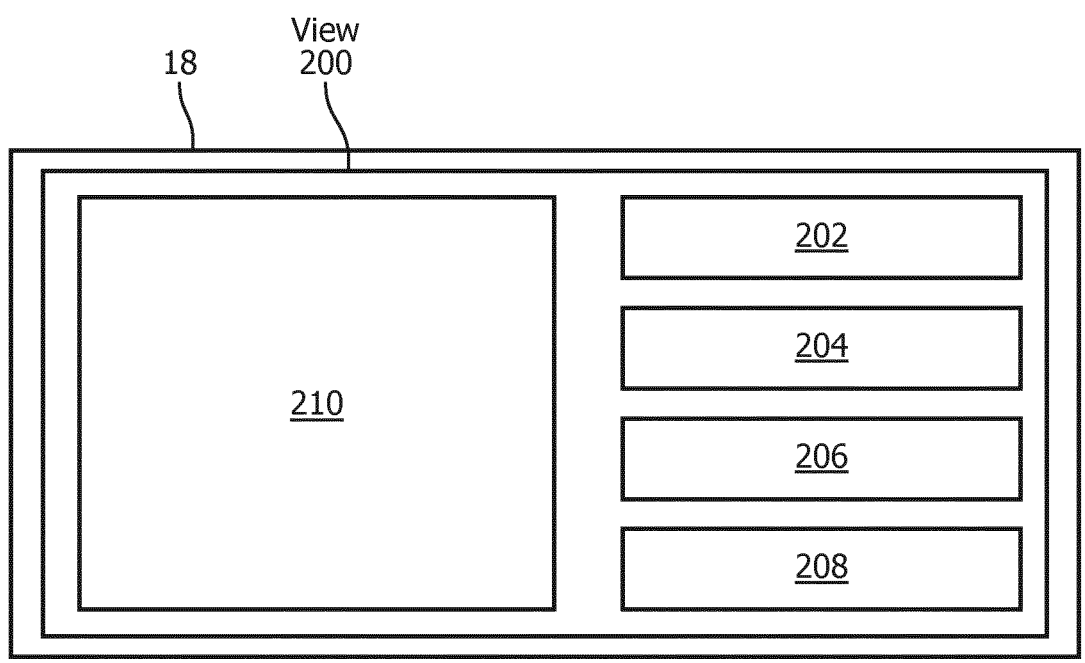
FIG. 2 illustrates a computing device and a view of a graphical user interface.
Figure 3:
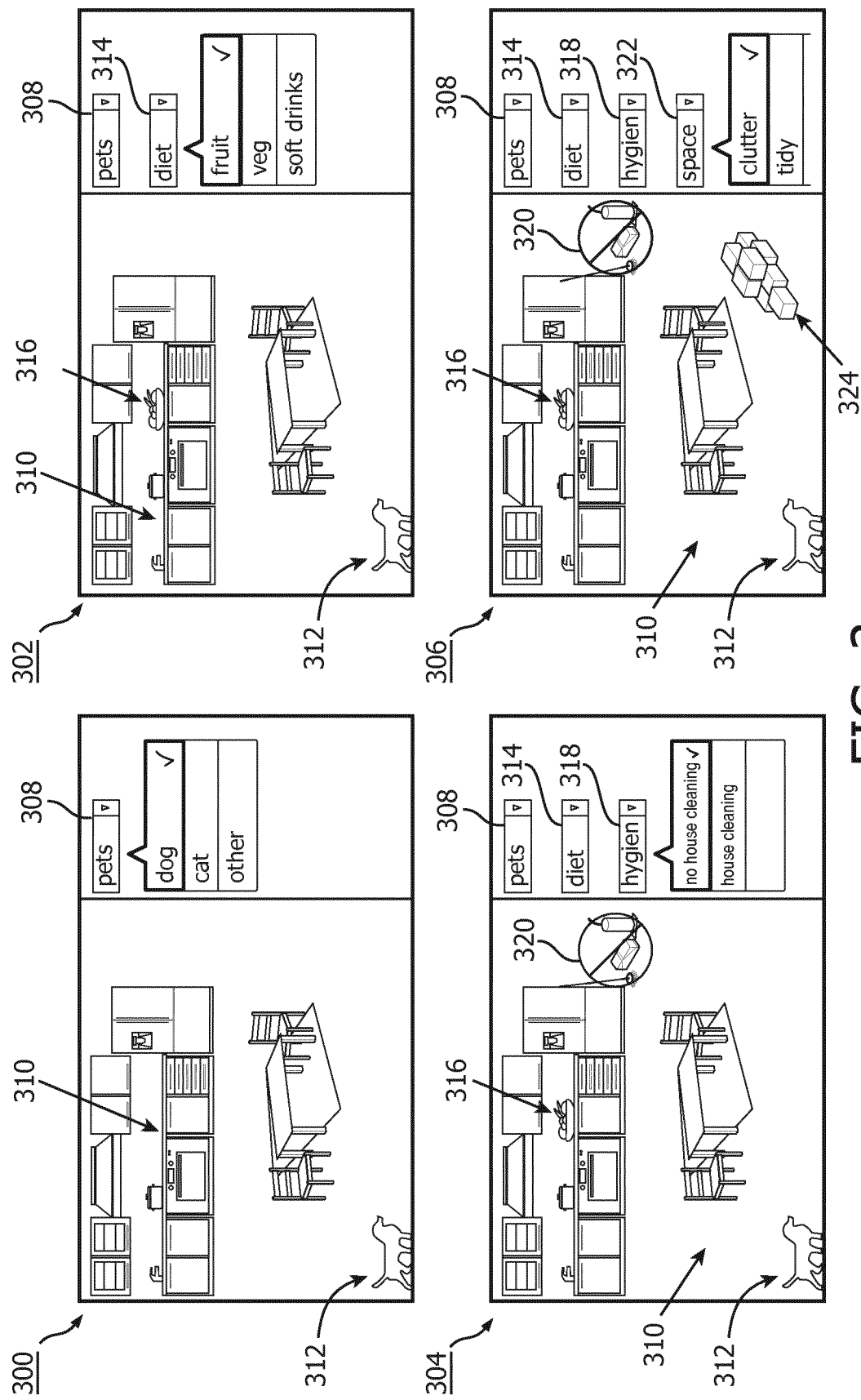
FIG. 3 illustrates additional example views of the graphical user interface.

FIG. 2 and FIG. 3 illustrate functions performed by graphical user interface component 30, observation component 32 and/or virtual representation component 34. For example, FIG. 2 illustrates computing device 18 and a view 200 of the graphical user interface. View 200 comprises observation fields 202, 204, 206, and 208 configured to receive entry and/or selection of the home health observations from caregiver 10 (FIG. 1) about conditions in home 12 (FIG. 1) of subject 14 (FIG. 1) and a display field 210 configured to display a virtual representation of the home conditions to caregiver 10. In some embodiments, observation fields 202-208 are configured as drop down boxes so caregiver 10 may select information about home 12, as textual entry fields so caregiver 10 may type, dictate, and/or otherwise enter information about home 12, and/or as other observation field types. In some embodiments, one or more observation fields 202-208 may be associated with one or more sensors 20 and configured to receive entry and/or selection of information related to sensed conditions of home 12 (described herein). Display field 210 may display a virtual representation of the home conditions generated (e.g., by virtual representation component 34 shown in FIG. 1) based on the home health observations received via fields 202-208, information from sensors (e.g., sensors 20 shown in FIG. 1), and/or other information.

FIG. 3 illustrates additional example views 300, 302, 304, 306 of the graphical user interface. View 300 comprises a "pets" observation field 308 comprising a drop down box configured to receive selection of what if any pets are present in home 12 (FIG. 1). View 300 further comprises display field 310 which displays a virtual image representative of the environment of home 12 including a dog 312 which was selected via observation field 308. View 302 comprises a "diet" observation field 314 comprising a drop down box configured to receive selection of what if any diet information is observable in home 12. Field 310 in view 302 displays the fruit 316 selected via field 314. View 304 comprises a "hygiene" observation field 318 comprising a drop down box configured to receive selection of what if any hygiene information is observable in home 12. Field 310 in view 304 displays the needed house cleaning 320 selected via field 318. View 306 comprises a "space" observation field 322 comprising a drop down box configured to receive selection of what if any space clutter information is observable in home 12. Field 310 in view 306 displays the clutter 324 selected via field 322.

Returning to FIG. 1, subject profile component 36 is configured to electronically store the home health observations and the virtual representation. In some embodiments, the home health observations and the virtual representation are stored in a subject profile for subject 14 that is part of a database (and/or a plurality of databases, the description of a database is not intended to be limiting) of previous home health observations and previous virtual representations for a plurality of subjects. The database may be stored, for example, in electronic storage 26, stored by external resources 28, and/or by other storage devices. In some embodiments, the subject profile includes information identifying subject 14 (e.g., a username, a number, an identifier, and/or other identifying information), security login information (e.g., a login code or password), demographic information (e.g., age, gender, ethnicity, residence location, etc.) associated with subject 14, information previously shared by subject 14 (e.g., answers to questionnaires, answers to questions at previous doctor's office visits, etc.), a medical history of subject 14, medical treatment facilities and/or staff who have treated subject 14, a current medical status of subject 14, a care plan for subject 14, and/or other information related to subject 14. Home health observations and virtual representations for other subjects stored in the database may be associated with corresponding subject profiles in the database for the other subjects.

Comparison component 38 is configured to compare the home health observations and virtual representation for home 12 of subject 14 to previous home health observations and previous virtual representations for similar subjects in the database. In some embodiments, comparison component 38 is configured to determine whether subjects are similar based on the information in the subject profiles and/or previously stored home health observations and/or virtual representations for the other subjects, and/or other information. For example, similar subjects may include subjects with a similar medical history; subjects who share a similar care plan; subjects of similar age, gender, and/or ethnicity; subjects who live near each other; subjects treated by the same medical facilities, doctors, and/or nurses; subjects whose homes share similar characteristics; and/or other characteristics.

In some embodiments, comparison component 38 is configured such that comparing the home health observations and virtual representation for home 12 of subject 14 to previous home health observations and previous virtual representations for similar subjects in the database is performed based on one or more matching algorithms. In some embodiments, based on the one or more matching algorithms, comparison component 38 matches subject 14 and/or the conditions in home 12 of subject 14 with other subjects and/or the homes of other subjects; determines whether the home conditions of subject 14 are improved, typical, and/or lacking relative to the home conditions of other subjects; identifies key individual differences between the home conditions of subject 14 and the home conditions of other subjects; identifies key individual similarities between the home conditions of subject 14 and the home conditions of other subjects; identifies differences in home conditions for subjects who share similar care plans; identifies similarities in home conditions for subjects who share similar care plans; and/or performs other operations. In some embodiments, comparison component 38 is configured to compare the subject's home environment from previous visits to the subject's home environment during the current visit, e.g. to observe changes in lifestyle or habits of subject 14 which may indicate a change in condition.

In some embodiments, comparison component 38 is configured such that comparing the home health observations and virtual representation for home 12 of subject 14 to previous home health observations and previous virtual representations for similar subjects in the database includes determining a similarity metric. The similarity metric is indicative of similarity between virtual representations, subject clinical status, subject care plans, and/or other information between subject 14 and other subjects. In some embodiments, the similarity metric is an alphanumeric indicator (e.g., a number, a letter, etc.) configured to indicate a degree to which a virtual representation, a clinical status, a care plan, and/or other information for subject 14 substantially matches a virtual representation, a clinical status, a care plan, and/or other information for one or more other subjects. In some embodiments, the similarity metric compares two vectors of virtual representations with each other. The distance and/or similarity between two of these vectors is computed by assigning a weight to each of the indicators. Higher weights indicate higher importance of the indicator, and contribute more to the computed similarity between two representations. The weights can be fixed and/or can be adapted based on boundary conditions. For example, for subjects with certain conditions (e.g. COPD) some representations (e.g. presence of pets or dust) can be deemed more important. Hence, based on the profile of the subject, the collection of observations/representations related to pets and/or dust is selective weighted more heavily in this scenario.

Recommendation component 40 is configured to determine suggested questions for subject 14, update a care plan for subject 14, determine health care recommendations for subject 14, and/or perform other operations. The suggested questions are configured to elicit information from subject 14 that furthers the knowledge of caregiver 10 about subject 14 that may be stored in system 8. Information gleaned from answers to the suggested questions may facilitate better care of subject 14 and/or have other effects. For example, the information in the answers to the suggested questions may be stored by system 8 and shared among peer caregivers who all care for subject 14 so that the individual care givers have the same information, may be used to better focus the current and/or future home visits with subject 14 to medical issues of greatest concern to subject 14, may be used to update a care plan for subject 14, may be used during care of similar subjects whose caregivers also utilize system 8, and/or may be used for other purposes. The suggested questions are determined based on the home health observations by caregiver 10, based on the virtual representation of home 12, based on the information in the subject profile, based on the comparison, and/or based on other information. For example, for a subject 14 whose subject profile in system 8 shows a history of sleep issues, and whose home health observations by caregiver 10 and/or virtual representation of home 12 reveal an uncomfortable and/or noisy sleep area in home 12, recommendation component 40 may recommend that caregiver 10 ask questions of subject 14 that delve more deeply into the sleep habits of subject 14. In some embodiments, graphical user interface component 30 is configured to cause display of the suggested questions to caregiver 10 and/or other caregivers via the graphical user interface. In some embodiments, graphical user interface component is configured to cause display of the suggested questions while caregiver 10 is in home 12 and/or at other times.

In some embodiments, determining suggested questions for subject 14 includes determining recommended observations that should be made by caregiver 10 and/or other indications of focus for caregiver 10 while visiting home 12. Recommendation component 40 may recommend further areas of home 12 caregiver 10 should observe; more detailed observations related to things like hygiene, clutter, diet, etc.; more detailed observations related to behavior of other occupants (e.g., people and/or animals) of home 12; and/or other areas for observation and/or focus. For example, if caregiver 10 observes and records as one of the home health observations sugary fruit juice, cookies, and a soda sitting out on a counter top, and the subject profile of subject 14 indicates that subject 14 has a medical condition that may require the dietary limitation of sugar, recommendation component 40 may recommend a closer inspection of food storage areas (e.g., cabinets, the refrigerator) to determine whether there are more sugary food items in home 12.

As described above, recommendation component 40 is configured to determine health care recommendations and update a care plan for subject 14. The health care recommendations may include recommended changes to the diet and/or exercise of subject 14, recommended changes to the environment inside home 12 (e.g., airflow, temperature, air quality), changes to sleeping patterns, a recommendation for care assistance, a recommendation for further assessments to be carried out, and/or other recommendations. The care plan for subject 14 may indicate a domestic care (e.g., in home) care schedule for subject 14, medications taken by subject 14, actions previously taken and/or actions that should be taken by caregiver 10 and/or other caregivers (e.g., a domestic/home caregiver) and/or subject 14 to care for subject 14 (e.g., living assistance tasks, visits to doctors, following a prescribed diet, following an exercise plan, following a sleep plan, heath education courses that subject 14 is to attend, etc.), tests and/or procedures performed and/or that will be performed on subject 14, and/or other care activities. In some embodiments, recommendation component 40 is configured to provide decision support to caregiver 10 and/or other caregivers for manual updates (e.g., by caregiver 10) to the care plan. In some embodiments, the care plan for subject 14 is stored in the subject profile (e.g., in electronic storage 26 and/or external resources 28). In some embodiments, the health care recommendations are determined and the care plan for subject 14 is updated based on the home health observations, the virtual representation, the comparison, information in the subject profile for subject 14 (e.g., a medical history of subject 14 including a current clinical status), and/or other information.

Figure 4:
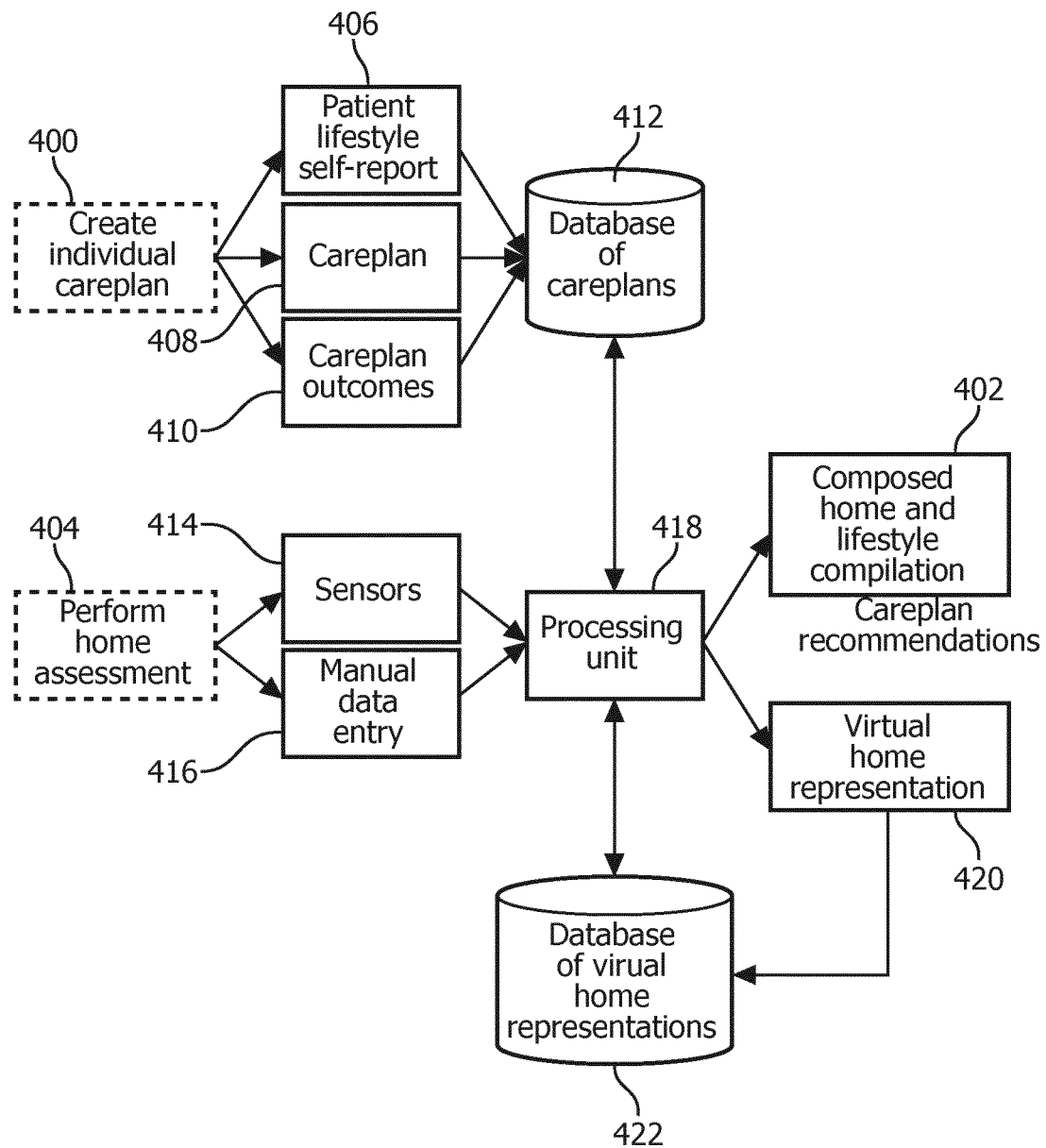
FIG. 4 summarizes elements of the system.

FIG. 4 summarizes elements of system 8 described herein. For example, FIG. 4 illustrates creating and/or updating a care plan 400, 402 based on a home assessment 404. Patient lifestyle self-reported information 406, a previously determined care plan 408, and desired care plan outcomes 410 for subject 14 (FIG. 1) may all be stored in a database of care plans 412 (e.g., electronic storage 26 and/or external resources 28 shown in FIG. 1). Home assessment 404 may be performed based on sensor information 414 (e.g., from sensors 20 shown in FIG. 1) and manual data entry and/or selection 416 (e.g., the home health observations made by caregiver 10 shown in FIG. 1). This information may be received by a processing unit 418 (e.g., processor 16 shown in FIG. 1) which is configured to generate a virtual representation 420 of the home conditions, compare the home health observations and virtual representation to previous home health observations and previous virtual representations for similar subjects in a database 422 (though this database may be the same as database 412), determine health recommendations for communication to the subject, and update a care plan 402 for the subject.

Figure 5:
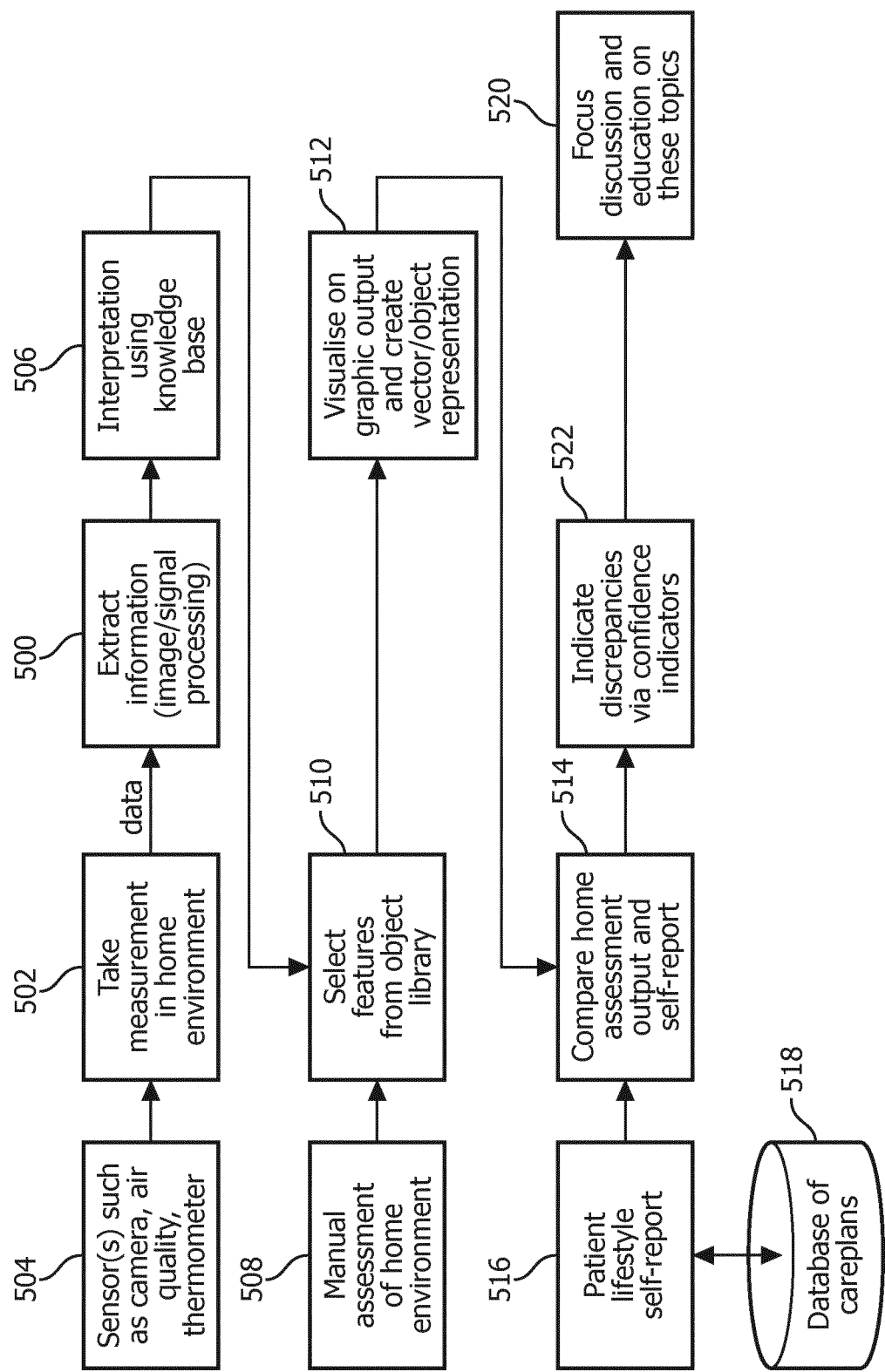
FIG. 5 illustrates an example of a way the system is configured to facilitate a focused discussion with, and education of, the subject based on information gathered at the home of the subject.

FIG. 5 illustrates an example of a way system 8 (FIG. 1) is configured to facilitate a focused discussion with, and education of, subject 14 (FIG. 1) based on information gathered at home 12 (FIG. 1). FIG. 5 illustrates extracting information 500 from measurements taken in the home (e.g., home 12) environment 502 by sensors 504 (e.g., sensors 20) such as a camera, an air quality sensor, and a thermometer. This information is interpreted 506 (e.g., by processor 16) along with a manual assessment of the home environment 508 (e.g., the home health observations by caregiver 10) to select features 510 for display in a virtual representation of the home of the subject 512. The system (e.g., processor 16 shown in FIG. 1) uses the information used to generate virtual representation 512 to compare 514 the home environment to self-reported information 516 from the subject (which, for example, may be accessed via a database of care plans 518 that is the same as or similar to the subject profile stored in electronic storage 26 and/or external resources 28). In this example, the system is configured to facilitate a focused discussion 520 of differences between the self-reported information and the information gathered during the home visit. In some embodiments, the discrepancies may be indicated 522 via confidence indicators and/or in other ways. In some embodiments, facilitating the focused discussion may include facilitating education of the subject, recommending questions to ask the subject, recommending closer investigation (e.g., making more home health observations) of various portions of the home of the subject, and/or other activities.

Figure 6:
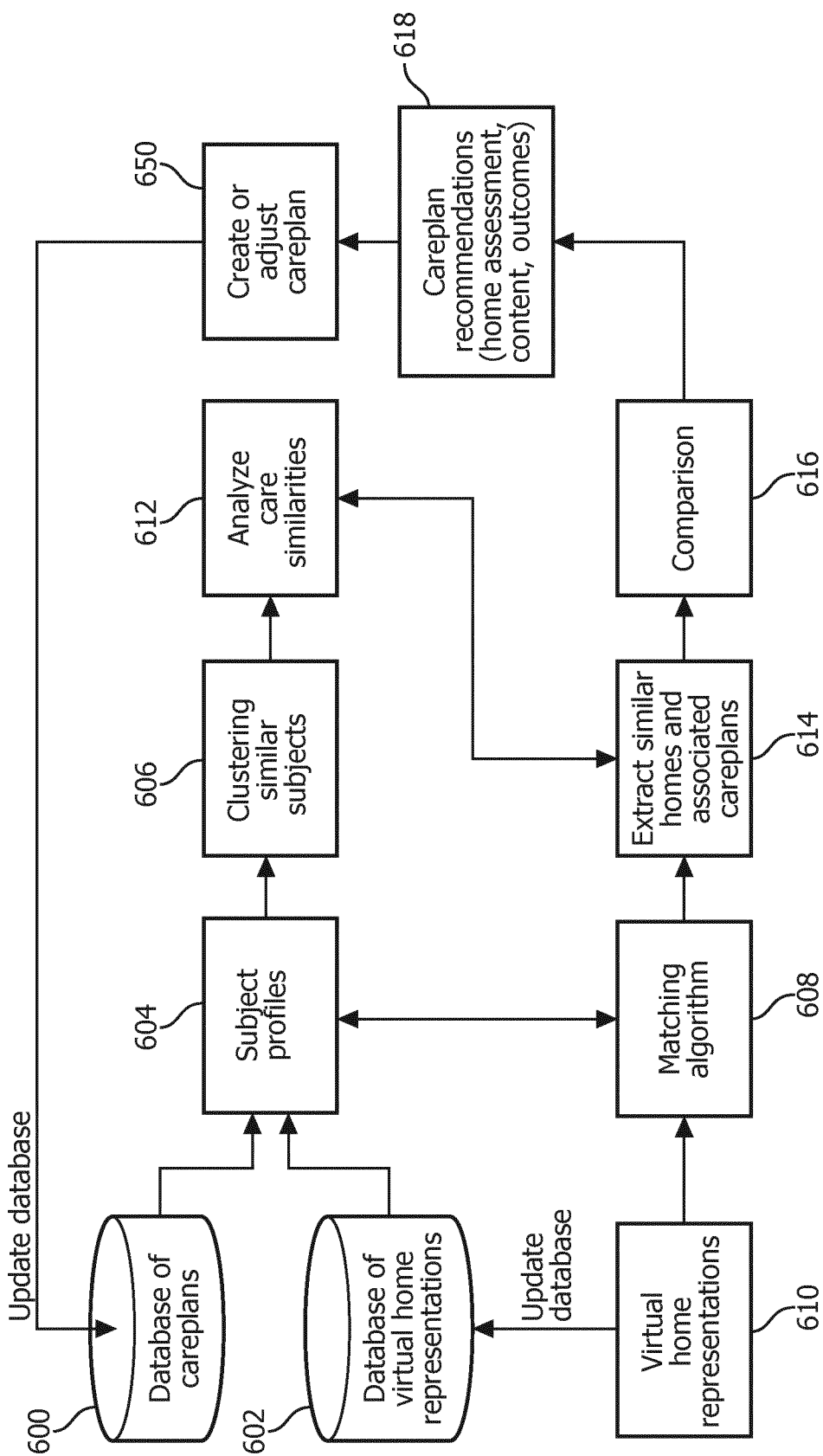
FIG. 6 illustrates updating a care plan for the subject.

FIG. 6 illustrates updating a care plan 650 for a subject (e.g., subject 14 shown in FIG. 1). FIG. 6 illustrates preexisting databases 600, 602 of care plans and virtual home representations (e.g., which may be and/or be stored in electronic storage 26 and/or external resources 28 shown in FIG. 1). This information may be included in a subject profile 604 for the subject, for example. Similar subjects (e.g., based on medical condition, demographics, etc.) may be clustered 606. Part of the clustering may be based on subjects who have substantially matching 608 virtual home representations 610. The clustered subjects are analyzed 612 to extract 614 information about subjects with similar living conditions and care plans so the home environments and care plans of these subjects with similarities can be compared 616. The system is configured to determine recommendations 618 for the subject based on this comparison and/or other information (e.g., as described herein). The care plan for the subject may be adjusted (and/or created for the first time) 650 based on recommendations 618.

Returning to FIG. 1, computing device 18 is configured to provide an interface between caregiver 10 and/or other users and system 8. Computing device 18 is configured to provide information to and/or receive information from caregiver 10 and/or other users. For example, computing device 18 is configured to present the graphical user interface to caregiver 10. In some embodiments, computing device 18 is configured to provide the graphical user interface, processing capabilities, databases, and/or electronic storage to system 8. As such, computing device 18 may include processor 16, electronic storage 26, external resources 28, and/or other components of system 8. In some embodiments, computing device 18 is connected to a network (e.g., the internet). In some embodiments, computing device 18 does not include processor 16, electronic storage 26, external resources 28, and/or other components of system 8, but instead communicates with these components via the network. The connection to the network may be wireless or wired. For example, processor 16 may be located in a remote server and graphical user interface component 30 may wirelessly cause display of the graphical user interface to caregiver 10 on computing device 18. In some embodiments, computing device 18 is coupled to sensor 20 and/or other components of system via the network. In some embodiments, computing device 18 is a laptop, a personal computer, a smartphone, a tablet computer, and/or other computing devices. Examples of interface devices suitable for inclusion in computing device 18 include a touch screen, a keypad, touch sensitive and/or physical buttons, switches, a keyboard, knobs, levers, a display, speakers, a microphone, an indicator light, an audible alarm, a printer, and/or other interface devices. The present disclosure also contemplates that computing device 18 includes a removable storage interface. In this example, information may be loaded into computing device 18 from removable storage (e.g., a smart card, a flash drive, a removable disk) that enables caregiver 10 and/or other users to customize the implementation of computing device 18. Other exemplary input devices and techniques adapted for use with computing device 32 include, but are not limited to, an RS-232 port, RF link, an IR link, a modem (telephone, cable, etc.) and/or other devices.

Sensor 20 is configured to generate output signals conveying information related to physical conditions present in home 12 of subject 14, and/or other information. In some embodiments, the output signals are received by processor 16, stored in electronic storage 26, received and stored by one or more servers included in external resources 28, and/or communicated to other devices. Information related to physical conditions present in home 12 may include images (e.g., visual, infrared, etc.) of home 12, a temperature of home 12, an air quality of the air in home 12, an airflow in home 12, a composition of the air in home 12, information related to motion of people, animals, and/or other objects in home 12, a humidity in home 12, information related to smells in home 12, information related to clutter in home 12, information related to presence of furniture and/or other objects in home 12, physical distances in home 12 (e.g., a distance of a route between bed and a bathroom), information related to tortuosity of various commonly traveled routes within home 12 (e.g., a tortuosity of the route between bed and the bathroom), and/or other information.

Sensor 20 may comprise one or more sensors that measure such physical conditions and/or physiological parameters directly. For example, sensor 20 may be and/or include a camera 22 positioned in home 12 configured to generate visual images of the interior of home 12, an air quality sensor 24 configured to generate output signals that conveys information related to an air quality in home 12, and/or other sensors. Sensor 20 may comprise one or more sensors that generate output signals conveying information related to the conditions in home 12 indirectly. For example, one or more sensors 20 may generate an output with air temperature, humidity, and/or flow information based on operation of a home ventilation system (e.g., a central heating/air conditioning system). In some embodiments, sensor 20 may be and/or include one or more of camera 22, air quality sensor 24, a temperature sensor, a humidity sensor, an air flow rate sensor, a gas composition sensor, a motion sensor, and/or other sensors.

Although sensor 20 is illustrated in FIG. 1 as camera 22 and air quality sensor 24 at two locations inside home 12, this is not intended to be limiting. Sensor 20 may include one or more sensors disposed in a plurality of locations, such as for example, within and/or in communication with a smartphone associated with subject 14, coupled (in a removable manner) with clothing of subject 14, worn by subject 14 (e.g., as a headband, wristband, etc.), positioned to point at subject 14 and/or areas inside and/or outside home 12, mounted on one or more surfaces in home 12, and/or in other locations. In addition, sensors 20 may include any type of sensor configured to generate output signals that convey information related to conditions inside home 12 and should not be limited to only the examples described above. In some embodiments, system 8 may not include sensors 20.

Electronic storage 26 comprises electronic storage media that electronically stores information. The electronic storage media of electronic storage 26 may comprise one or both of system storage that is provided integrally (i.e., substantially non-removable) with system 8 and/or removable storage that is removably connectable to system 8 via, for example, a port (e.g., a USB port, a firewire port, etc.) or a drive (e.g., a disk drive, etc.). Electronic storage 26 may be (in whole or in part) a separate component within system 8, or electronic storage 26 may be provided (in whole or in part) integrally with one or more other components of system 8 (e.g., computing device 18, processor 16, etc.). In some embodiments, electronic storage 26 may be located in a server together with processor 16, in a server that is part of external resources 28, in computing device 18 associated with caregiver 10, and/or other users, and/or in other locations. Electronic storage 26 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 26 may store software algorithms, information determined by processor 16, information received via computing device 18 and/or other external computing systems, information received from external resources 28, information received from sensors 20, and/or other information that enables system 8 to function as described herein. By way of a non-limiting example, electronic storage 26 may store the user profile for subject 14, the home health observations and virtual representations for subject 14 and other subjects, and/or other information.

External resources 28 include sources of information (e.g., databases, websites, etc.), external entities participating with system 8 (e.g., a medical records system of a health care provider that stores a health plan for subject 14), external home monitoring systems, one or more servers outside of system 8, a network (e.g., the internet), electronic storage, equipment related to Wi-Fi technology, equipment related to Bluetooth® technology, data entry devices, sensors, scanners, computing devices associated with individual users, and/or other resources. For example, in some embodiments, external resources 28 may include the database where the home health observations and the virtual representations for subject 14 and/or other subjects are stored, and/or other sources of information. In some implementations, some or all of the functionality attributed herein to external resources 28 may be provided by resources included in system 8. External resources 28 may be configured to communicate with processor 16, computing device 18, sensor 20, electronic storage 26, and/or other components of system 8 via wired and/or wireless connections, via a network (e.g., a local area network and/or the internet), via cellular technology, via Wi-Fi technology, and/or via other resources.

Figure 7:
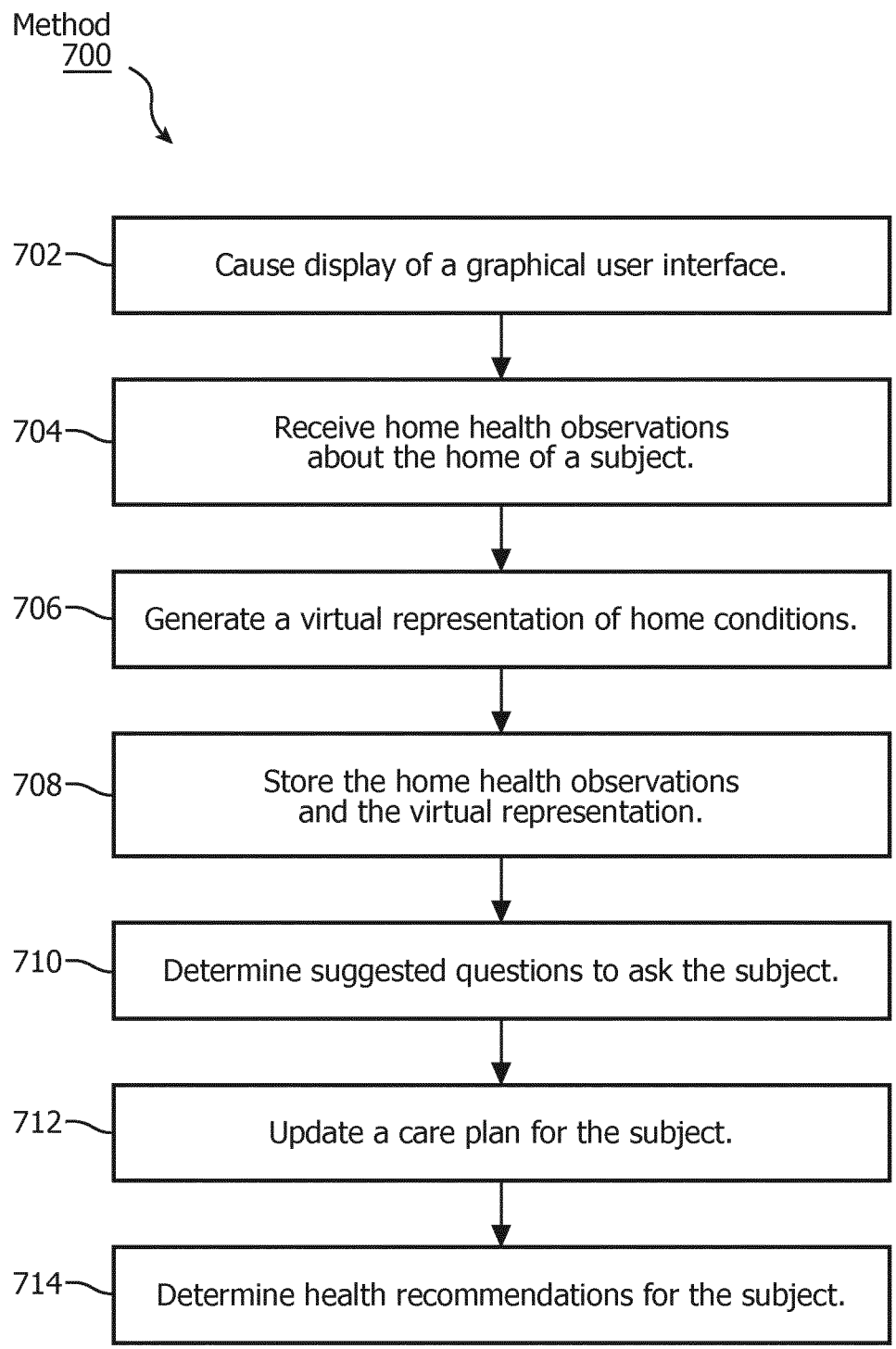
FIG. 7 illustrates a method for standardizing collection of home health observations.

FIG. 7 illustrates a method 700 for standardizing collection of home health observations with a standardization system made during a home visit by a caregiver to a home of a subject. The system comprises one or more hardware processors and/or other components. The one or more hardware processors are configured by machine readable instructions to execute computer program components. The computer program components comprise a graphical user interface component, an observation component, a virtual representation component, a subject profile component, a comparison component, a recommendation component, and/or other components. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, a graphical user interface is displayed to the caregiver. The graphical user interface is displayed on a computing device associated with the caregiver while the caregiver is in the home of the subject. The graphical user interface comprises one or more observation fields configured to receive entry and/or selection of the home health observations from the caregiver about conditions in the home of the subject, a display field configured to display a virtual representation of the home conditions to the caregiver, and/or other fields. In some embodiments, operation 702 is performed by a processor component the same as or similar to graphical user interface component 30 (shown in FIG. 1 and described herein).

At an operation 704, home health observations about the home of the subject are received from the caregiver. The home health observations are received via the one or more observation fields of the graphical user interface. In some embodiments, receiving the home health observations includes receiving information related to a diet of the subject, hygiene of the subject, whether the subject or another occupant of the home smokes, presence of clutter in the home, presence of pets in the home, safety hazards in the home, and/or other characteristics of the home environment of the subject. In some embodiments, operation 704 may include generating, with one or more sensors, output signals that convey information related to physical conditions present in the home of the subject. For example, the one or more sensors may comprise a camera configured to generate images of the home, an air quality sensor configured to generate output signals conveying information related to air quality in the home, and/or other sensors. In some embodiments, operation 704 is performed by a processor component the same as or similar to observation component 32 and/or sensors the same as or similar to sensors 20 (shown in FIG. 1 and described herein).

At an operation 706, a virtual representation of conditions in the home is generated. The virtual representation of conditions in the home is generated for display to the caregiver via the display field of the graphical user interface. The virtual representation is generated based on the home health observations, the output signals, and/or other information. The virtual representation of the home conditions comprises an aggregation of the home health observations. In some embodiments, operation 706 is performed by a processor component the same as or similar to virtual representation component 34 (shown in FIG. 1 and described herein).

At an operation 708, the home health observations and the virtual representation are stored. In some embodiments, the home health observations and the virtual representation are stored in a subject profile for the subject that is part of a database of previous home health observations and previous virtual representations for a plurality of subjects. In some embodiments, operation 708 is performed by a processor component the same as or similar to subject profile component 36 (shown in FIG. 1 and described herein).

At an operation 710, suggested questions for the subject are determined. In some embodiments, operation 710 includes comparing the home health observations and virtual representation to previous home health observations and previous virtual representations for similar subjects in the database. The suggested questions are determined based on information in the subject profile, based on the comparison, and/or based on other information. In some embodiments, operation 710 includes causing display of the suggested questions to the caregiver via the graphical user interface while the caregiver is in the home. In some embodiments, operation 710 is performed by processor components the same as or similar to graphical user interface component 30, comparison component 38, and/or recommendation component 40 (shown in FIG. 1 and described herein).

At an operation 712, a care plan for the subject is updated. In some embodiments, the care plan for the subject is stored in the subject profile. In some embodiments, the care plan for the subject is updated based on the home health observations, the virtual representation, the comparison, and/or other information. In some embodiments, operation 712 is performed by a processor component the same as or similar to recommendation component 40 (shown in FIG. 1 and described herein).

At an operation 714, heath care recommendations for the subject are determined. The health care recommendations are determined based on information in the subject profile, the updated care plan, the comparison, the home health observations, the virtual representation, and/or other information. In some embodiments, operation 714 is performed by a processor component the same as or similar to recommendation component 40 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to standardize collection of home health observations made during a home visit by a caregiver to a home of a subject, the system comprising;
one or more sensors in a home environment of the subject, the one or more sensors including at least one image sensor configured to obtain images related to physical conditions present in the home environment of the subject;
an environmental sensor configured to obtain environmental information about the home environment, wherein the environmental information is one or more of air quality, temperature, humidity, air flow, and gas composition;
a motion sensor configured to obtain motion information within the home environment, wherein the motion information is motion of the subject or a pet; and
a computing device associated with the caregiver, the computing device comprising a display, and further comprising one or more hardware processors configured by machine-readable instructions to:
cause display of a graphical user interface to the caregiver on the display of the computing device associated with the caregiver while the caregiver is in the home of the subject, the graphical user interface comprising:
one or more observation fields configured to receive entry and/or selection of the home health observations from the caregiver about conditions in the home of the subject, and
a display field configured to display a virtual representation of a home environment of the subject to the caregiver;
receive the home health observations from the caregiver via the one or more observation fields, the home health observations being characteristics of the home environment of the subject;
obtain one or more output signals from the one or more sensors, the environmental sensor, and the motion sensor;
detect, within one or more of the images in the received output signals from the one or more sensors, objects or areas of interest including one or more objects within the home environment of the subject;
determine associations between the home health observations and the detected objects or areas of interest within the home environment;
generate, based on the images, the received one or more output signals from the environmental sensor and the motion sensor, and the home health observations, the virtual representation of the home environment of the subject for display to the caregiver via the display field, the virtual representation comprising a visualization of the objects positioned with respect to each other within the home;
visually alter, by highlighting, the visualization of at least one of the detected objects or areas of interest in the home environment based on the associations determined between the home health observations and the detected objects or areas of interest within the home environment;
determine, based on the generated virtual representation and the received home health observations, suggested questions for the caregiver to elicit information from the subject; and
cause the graphical user interface to display the suggested questions while the care giver is in the home.

2. The system of claim 1, wherein the one or more hardware processors are configured such that receiving the home health observations includes receiving information related to one or more of a diet of the subject, hygiene of the subject, whether the subject or another occupant of the home smokes, presence of clutter in the home, presence of pets in the home, or safety hazards in the home.

3. The system of claim 1, wherein the one or more hardware processors are further configured to:
store the home health observations and the virtual representation in a subject profile for the subject that is part of a database of previous home health observations and previous virtual representations for a plurality of subjects;

compare the home health observations and virtual representation to previous home health observations and previous virtual representations for similar subjects in the database;

determine the suggested questions for the caregiver to ask the subject based on information in the subject profile and based on the comparison; and cause display of the suggested questions to the caregiver via the graphical user interface while the caregiver is in the home.

4. The system of claim 3, wherein the one or more hardware processors are further configured to:

update a care plan for the subject stored in the subject profile based on the home health observations, the virtual representation, and the comparison; and determine health recommendations for communication to the subject based on information in the subject profile, the updated care plan, the comparison, the home health observations, and the virtual representation.

5. The system of claim 1, wherein detecting the one or more objects or areas of interest including one or more objects comprises:

detecting, in an image, an object or area of interest comprising one or more objects based on one or more of contrast, brightness, or edge detection filtering of the image.

6. A method for standardizing collection of home health observations with a standardization system made during a home visit by a caregiver to a home of a subject, the system comprising: (i) one or more sensors in a home environment of the subject, the one or more sensors including at least one image sensor configured to obtain images related to physical conditions present in the home environment of the subject (ii) an environmental sensor configured to obtain environmental information about the home environment, wherein the environmental information is one or more of air quality, temperature, humidity, air flow, and gas composition (iii) a motion sensor configured to obtain motion information within the home environment, wherein the motion information is motion of the subject or a pet, and (iv) a computing device associated with the caregiver, the computing device comprising a display, and further comprising one or more hardware processors, the method comprising:

causing, with the one or more hardware processors, display of a graphical user interface to the caregiver on the display of the computing device associated with the caregiver while the caregiver is in the home of the subject, the graphical user interface comprising:

one or more observation fields configured to receive entry and/or selection of the home health observations from the caregiver about conditions in the home of the subject, and a display field configured to display a virtual representation of a home environment to the caregiver;

receiving, with the one or more hardware processors, the home health observations from the caregiver via the one or more observation fields, the home health observations being characteristics of the home environment of the subject;

obtaining, with the one or more hardware processors, one or more output signals from one or more sensors, the environmental sensor, and the motion sensor;

detecting, with the one or more hardware processors, within one or more of the images in the received output signals from the one or more sensors, objects or areas of interest including one or more objects within the home environment of the subject;

determining, with the one or more hardware processors, associations between the home health observations and the detected objects or areas of interest within the home environment;

generating, with the one or more hardware processors, based on the images, the received one or more output signals from the environmental sensor and the motion sensor, and the home health observations, the virtual representation of the home environment for display to the caregiver via the display field, the virtual representation comprising a visualization of the objects positioned with respect to each other within the home;

visually altering, by highlighting, the visualization of at least one of the detected objects or areas of interest in the home environment based on the associations determined between the home health observations and the detected objects or areas of interest within the home environment;

determining, based on the generated virtual representation and the received home health observations, suggested questions for the caregiver to elicit information from the subject; and causing the graphical user interface to display the suggested questions while the care giver is in the home.

7. The method of claim 6, wherein receiving the home health observations includes receiving information related to one or more of a diet of the subject, hygiene of the subject, whether the subject or another occupant of the home smokes, presence of clutter in the home, presence of pets in the home, or safety hazards in the home.

8. The method of claim 6, further comprising:

storing, with the one or more hardware processors, the home health observations and the virtual representation in a subject profile for the subject that is part of a database of previous home health observations and previous virtual representations for a plurality of subjects;

comparing, with the one or more hardware processors, the home health observations and virtual representation to previous home health observations and previous virtual representations for similar subjects in the database;

determining, with the one or more hardware processors, suggested questions for the caregiver to ask the subject based on information in the subject profile and based on the comparison; and causing, with the one or more hardware processors, display of the suggested questions to the caregiver via the graphical user interface while the caregiver is in the home.

9. The method of claim 8, further comprising:

updating, with the one or more hardware processors, a care plan for the subject stored in the subject profile based on the home health observations, the virtual representation, and the comparison; and determining, with the one or more hardware processors, health recommendations for communication to the subject based on information in the subject profile, the updated care plan, the comparison, the home health observations, and the virtual representation.

10. The method of claim 6, wherein detecting the one or more objects or areas of interest including one or more objects comprises:

detecting, in an image, an object or area of interest comprising one or more objects based on one or more of contrast, brightness, or edge detection filtering of the image.

11. The method of claim 10, wherein the one or more sensors further comprise an air quality sensor configured to generate output signals conveying information related to air quality in the home.

12. A system for standardizing collection of home health observations made during a home visit by a caregiver to a home of a subject, the system comprising:
   one or more sensors in a home environment of the subject, the one or more sensors including at least one image sensor configured to obtain images related to physical conditions present in the home environment of the subject;
   an environmental sensor configured to obtain environmental information about the home environment, wherein the environmental information is one or more of air quality, temperature, humidity, air flow, and gas composition;
   a motion sensor configured to obtain motion information within the home environment, wherein the motion information is motion of the subject or a pet;
   a computing device associated with the caregiver, the computing device comprising a non-transitory computer readable storage medium storing an executable program, a and further comprising a processor, and further comprising a user interface, wherein the user interface is configured to:
      receive entry and/or selection of the home health observations from the caregiver about conditions in the home of the subject, and
      display a virtual representation of a home environment of the subject to the caregiver; and
   the processor executing the executable program to cause the processor to:
      receive the home health observations from the caregiver via the one or more observation fields, the home health observations being characteristics of the home environment of the subject;
      obtain, via the one or more sensors in the home environment of the subject, images related to physical conditions present in the home environment of the subject;
      obtain one or more output signals from the environmental sensor and the motion sensor;
      detect, within obtained one or more of the images, objects or areas of interest including one or more objects within the home environment of the subject;
      determine associations between the home health observations and the detected objects or areas of interest within the home environment;
      generate the virtual representation of the home environment based on the images, the received one or more output signals from the environmental sensor and the motion sensor, and the home health observations field, the virtual representation comprising a visualization of the objects positioned with respect to each other within the home;
      visually alter, by highlighting, the visualization of at least one of the detected objects or areas of interest in the home environment based on the associations determined between the home health observations and the detected objects or areas of interest within the home environment;
      determine, based on the generated virtual representation and the received home health observations, suggested questions for the caregiver to elicit information from the subject; and
      cause the graphical user interface to display the suggested questions while the care giver is in the home.

13. The system of claim 12, wherein receiving the home health observations includes receiving information related to one or more of a diet of the subject, hygiene of the subject, whether the subject or another occupant of the home smokes, presence of clutter in the home, presence of pets in the home, or safety hazards in the home.

14. The system of claim 12, wherein the processor is further configured to:
   store the home health observations and the virtual representation in a subject profile for the subject that is part of a database of previous home health observations and previous virtual representations for a plurality of subjects;
   compare the home health observations and virtual representation to previous home health observations and previous virtual representations for similar subjects in the database;
   determine suggested questions for the caregiver to ask the subject based on information in the subject profile and based on the comparison; and
   display the suggested questions to the caregiver via the graphical user interface while the caregiver is in the home.

15. The system of claim 14, wherein the processor is further configured to:
   update a care plan for the subject stored in the subject profile based on the home health observations, the virtual representation, and the comparison; and
   determine health recommendations for communication to the subject based on information in the subject profile, the updated care plan, the comparison, the home health observations, and the virtual representation.

16. The system of claim 12, wherein the processor is further configured to:
   detect, in an image, an object or area of interest comprising one or more objects based on one or more of contrast, brightness, or edges.

17. The system of claim 1, wherein determining the suggested questions comprises:
   determining recommended observations to be made by caregiver.

18. The system of claim 1, wherein determining the suggested questions comprises:
   revealing an uncomfortable or noisy sleep area in home on the virtual representation; and
   recommending the caregiver to ask questions about sleep habits of the subject.

19. The system of claim 1, wherein the suggested questions relate to the conditions present in the home of the subject and relate to the associations of the home health observations and the objects in the home environment as displayed in the generated virtual representation.

20. The system of claim 1, wherein the one or more hardware processors are further configured to:
   compare the home health observations to self-reported information from the subject to determine discrepancies between the self-reported information and the home health observations,
   wherein the discrepancies between the self-reported information and the home health observations are then indicated via confidence indicators on the graphical user interface.

* * * * *